United States Patent [19]

Thompson et al.

[11] Patent Number: 5,368,570
[45] Date of Patent: Nov. 29, 1994

[54] APPARATUS FOR INFUSING MEDICAL SOLUTIONS

[75] Inventors: John Thompson, Rancho Santa Margarita; Charles R. Botts, San Diego, both of Calif.

[73] Assignee: Imed Corporation, San Diego, Calif.

[21] Appl. No.: 790,367

[22] Filed: Nov. 12, 1991

[51] Int. Cl.$^5$ ............................................. A61M 37/00
[52] U.S. Cl. ................................... 604/131; 604/132; 604/262; 604/142; 604/185
[58] Field of Search ................................. 604/131–134, 604/142, 185, 257–259, 262, 71, 80, 81; 222/94–96, 105, 106

[56] References Cited

U.S. PATENT DOCUMENTS

| | | |
|---|---|---|
| 7,816 | 12/1850 | Trotter . |
| 1,895,623 | 1/1933 | Hewitt . |
| 1,907,673 | 5/1933 | Rockwell . |
| 2,222,869 | 11/1940 | Jencick ........................ 103/150 |
| 2,471,796 | 10/1945 | Thiberg ........................ 230/170 |
| 2,764,942 | 10/1956 | Guarnaschelli et al. ........ 103/38 |
| 2,791,186 | 5/1957 | Alden ........................... 103/150 |
| 2,803,195 | 8/1957 | Lock ............................. 103/152 |
| 2,930,324 | 3/1960 | Toulmin, Jr. ................. 103/53 |
| 3,039,399 | 6/1962 | Everett ......................... 103/150 |
| 3,080,825 | 3/1963 | Guaraschelli et al. ......... 103/150 |
| 3,212,446 | 10/1965 | Golden et al. ................. 103/150 |
| 3,381,582 | 5/1968 | Golden .......................... 91/47 |
| 3,412,906 | 11/1968 | Dinger ........................... 222/183 |
| 3,416,461 | 12/1968 | McFarland ..................... 103/150 |
| 3,468,308 | 9/1969 | Bierman ........................ 128/214 |
| 3,469,578 | 9/1969 | Bierman ........................ 128/214 |
| 3,496,878 | 2/1970 | Hargest et al. ................ 103/152 |
| 3,506,005 | 4/1970 | Gilio et al. .................... 128/214 |
| 3,653,377 | 4/1972 | Rebold .......................... 128/66 |
| 3,672,543 | 6/1972 | Roper et al. ................... 222/183 |
| 3,677,444 | 8/1972 | Merrill .......................... 222/135 |
| 3,698,595 | 10/1972 | Gortz et al. ................... 220/63 R |
| 3,738,538 | 6/1973 | Roper et al. ................... 222/183 |
| 3,791,557 | 2/1974 | Venus, Jr. ..................... 222/105 |
| 3,796,356 | 3/1974 | Venus, Jr. ..................... 222/212 |
| 3,876,115 | 4/1975 | Venus, Jr. et al. ............. 222/183 |
| 3,907,169 | 9/1975 | Gortz et al. ................... 222/95 |
| 3,940,026 | 2/1976 | Kain ............................. 222/212 |
| 3,947,156 | 3/1976 | Becker .......................... 417/437 |
| 3,961,725 | 6/1976 | Clark ............................ 222/1 |
| 3,981,415 | 9/1976 | Fowler et al. ................. 222/95 |
| 4,140,117 | 2/1979 | Buckles ......................... 128/213 |
| 4,222,499 | 9/1980 | Lee et al. ...................... 222/183 |
| 4,318,400 | 3/1982 | Peery et al. ................... 128/214 |
| 4,324,350 | 4/1982 | Thompson ..................... 222/212 |
| 4,386,929 | 6/1983 | Peery et al. ................... 604/132 |

(List continued on next page).

FOREIGN PATENT DOCUMENTS 0399712 11/1990 European Pat. Off. ..... A61M 25/10
921181 7/1992 WIPO ........................... 604/131

OTHER PUBLICATIONS

The Aminoclycoside Delivery System, Infusions Systems Corporation.
The Homepump Family of Disposable Elastomeric Infusion Systems, McGaw, Inc.
Travenol Infusor Chemotherapy, Travenol.
Vs. Pharmacy Control, Baxter.

*Primary Examiner*—Randall L. Green
*Assistant Examiner*—Rob Clarke
*Attorney, Agent, or Firm*—Nydegger & Associates

[57] ABSTRACT

An IV infusion method and apparatus includes a plurality of fluid pumps mounted within a portable support housing and coupled to an IV tube. Each separate fluid pump is adapted to deliver fluid at a substantially constant delivery pressure predetermined by the characteristics of the pump. Each fluid pump includes an elastomeric membrane stretched into its region of nonlinear elasticity over a contour surface. Check valves located between the pumps and the IV tube control sequential dispensing of fluids from the pumps. The method and apparatus are especially adapted to a SASH process.

13 Claims, 5 Drawing Sheets

U.S. PATENT DOCUMENTS

| | | | |
|---|---|---|---|
| 4,411,603 | 10/1983 | Kell | 417/479 |
| 4,419,096 | 2/1983 | Leeper et al. | 604/132 |
| 4,446,991 | 5/1984 | Thompson | 222/94 |
| 4,458,830 | 7/1984 | Werding | 222/131 |
| 4,491,247 | 1/1985 | Nitchman et al. | 222/131 |
| 4,541,788 | 9/1985 | Nomura et al. | 417/471 |
| 4,573,883 | 3/1986 | Noon et al. | 417/394 |
| 4,702,397 | 10/1987 | Gortz | 222/211 |
| 4,734,008 | 9/1988 | Hessel | 604/132 |
| 4,734,092 | 3/1988 | Miller | 604/67 |
| 4,772,263 | 9/1988 | Dorman et al. | 604/132 |
| 4,925,444 | 5/1990 | Orkin et al. | 604/80 |
| 4,953,753 | 9/1990 | Gortz | 222/105 |
| 4,968,301 | 11/1990 | di Palma et al. | 604/132 |
| 5,013,303 | 5/1991 | Tamari et al. | 604/140 |
| 5,019,047 | 5/1991 | Kriesel | 604/132 |
| 5,167,631 | 12/1992 | Thompson et al. | 604/132 |
| 5,188,603 | 2/1993 | Vaillancourt | 604/131 |
| 5,298,025 | 3/1994 | Hessel et al. | 604/132 |

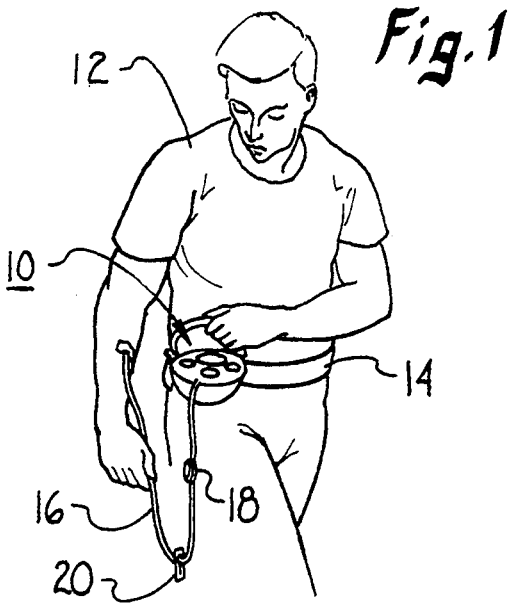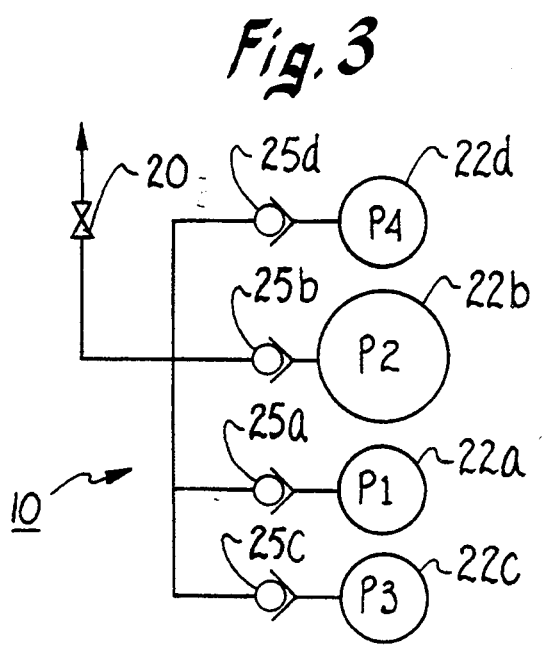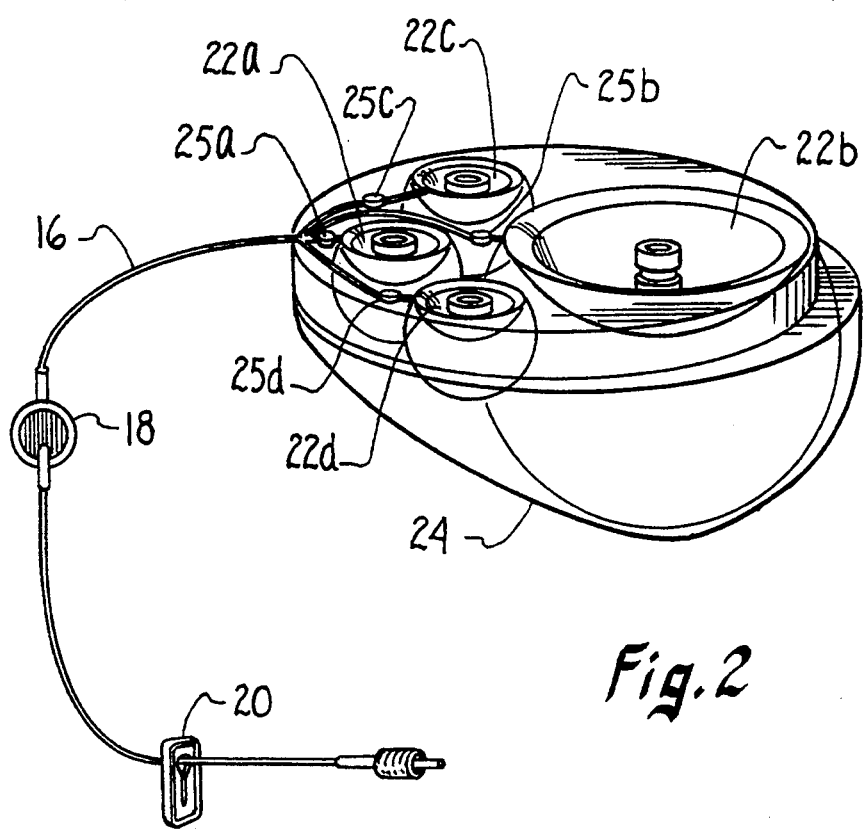

SEQUENTIAL DISCHARGE OF S.A.S.H. FLUIDS

APPARATUS FOR INFUSING MEDICAL SOLUTIONS

FIELD OF THE INVENTION

The present invention relates to methods and apparatus for infusing medical solutions in a predetermined sequence into patients. The present invention is particularly, but not exclusively, useful for infusing medical solutions in accordance with a SASH or SAS process automatically and in the correct sequence.

BACKGROUND OF THE INVENTION

Current intravenous IV site flushing techniques for antibiotics and other medicaments use saline and heparin solutions to maintain an IV site. One such technique is known in the art as a SASH process. The term SASH refers to the sequential infusion of a saline (S) solution for initially flushing an IV site, followed by the infusion of a medicant such as an antibiotic (A), followed by another saline (S) solution flush, and for those IV sites that require it a final infusion of a heparin (H) solution as an anti-coagulant. The dosage of the saline and of the heparin is typically in the range of 3-5 ml. The dosage of an antibiotic in a diluent may vary from about 20-250 ml.

In the past the SASH process has typically been performed using pre-filled medical syringes. This requires separate syringes each having a separate needle. Additionally, multiple site access and a sequential site cleaning are also required. This relatively complicated procedure is difficult for homecare and ambulatory patients to perform. It is critical that the procedure be carried out in a proper sequence to insure a non-clogged access to the IV site.

For maximum flexibility in the implementation of an extended and comprehensive infusion therapy program there is a recognized need for a SASH method and apparatus that can be performed by a greater number of untrained personnel such as outpatients. Preferably such a SASH method and apparatus could also be set up and operated by an ambulatory patient, with little or no additional training from medical personnel.

One such SASH delivery system that requires additional training is marketed by Block Medical, Inc. of Carlsbad, Calif. under the trademark of Auto-SASH ™. This system includes three separate reservoirs that contain two doses of a saline solution and one dose of a heparin solution. Each of the reservoirs is coupled to a single IV line and is discharged by a manually operated press pump formed integrally with the reservoir. The system is designed for treating an IV site while an antibiotic is being administered using a separate IV delivery system. Prior to dispensing of an antibiotic into the IV site the IV line of the Auto-SASH ™ is coupled to the site. A patient first dispenses a dose of saline solution into the site (for flushing the site) by manually pressing the press pump for that reservoir. The antibiotic is then dispensed followed by a dose of saline from the Auto-SASH ™. Finally, a dose of a heparin solution can be administered in the same manner. A deficiency of this prior art system is that a patient must manually discharge each valve in the proper sequence. This requires attentiveness and some training on the part of the patient. Additionally, this Auto-SASH ™ system must be used in combination with a separate delivery system, such as a pump or IV pole for the antibiotic. The present invention is directed to a portable SASH infusion apparatus and method that overcomes these prior art limitations.

In light of the above it is an object of the present invention to provide a method and apparatus to simply and safely infuse medical solutions in the proper sequence especially for a mobile or ambulatory patient. Another object of the present invention is to provide a method and apparatus for infusing medical solutions that can automatically dispense solutions in the proper sequence for a SASH process. Still another object of the present invention is to provide a portable IV infusion apparatus which provides for the complete discharge of separate solutions and for a substantially uniform delivery pressure for each separate solution. Yet another object of the present invention is to provide a portable IV infusion apparatus for multiple solutions which can be reused and pre-filled in a ready-to-use configuration for a relatively extended period of time while maintaining sterility of the solutions held in the apparatus. Another object of the present invention is to provide a portable IV infusion apparatus for multiple solutions in the proper sequence which is easy to use, relatively simple to manufacture and comparatively cost effective.

SUMMARY OF THE INVENTION

In accordance with the present invention a portable IV infusion apparatus includes a plurality of separate fluid pumps for sequentially dispensing medical solutions at different fluid delivery pressures to an IV site. In an illustrative embodiment for a SASH process four separate fluid pumps are mounted within a transportable support housing and are coupled to a single IV tube. The IV tube may include an on-off valve constructed as a conventional slide clamp. Each separate fluid pump is adapted to deliver solution at a delivery pressure pre-determined by the characteristics of the fluid pump. Check valves are located between the separate pumps for sequentially dispensing solution from each pump into the IV tube after the previous pump is emptied. In use, a patient may use the device by first priming the IV line, opening the on-off clamp to occlude the IV line, and then hooking the line to a venous access device. The infusion apparatus of the invention then automatically delivers the fluid solutions in a proper sequence as a result of the pre-determined delivery pressures of the infusion apparatus.

In a broad sense, the portable IV infusion pump may be loaded with the operative solutions at a hospital or pharmacy and is then adapted to dispense multiple solutions to an IV site by a method that generally stated includes the steps of:

1. connecting a first and a second reservoir to a single IV line;
2. pressurizing the first reservoir with a first fluid to a pressure of $P_1$ and completely discharging the first reservoir at a substantially constant delivery pressure;
3. pressurizing the second reservoir with a second fluid to a pressure of $P_2$ and completely discharging the second reservoir at a substantially constant delivery pressure with $P_1 > P_2$;
4. controlling fluid flow such that the first reservoir is completely discharged of fluid prior to the second reservoir initiating discharge of fluid and the second reservoir is then completely discharged of fluid.

For a SASH process four separate reservoirs are involved, a saline containing reservoir at a pressure of $P_1$, an antibiotic containing reservoir at a pressure of $P_2$, a saline containing reservoir at a pressure of $P_3$, and a heparin containing reservoir at a pressure of $P_4$, with $P_1 > P_2 > P_3 > P_4$. (For a SAS process three separate reservoirs are required.) For sequentially controlling flow from the separate reservoirs into the IV tube, check valves may be located between the reservoirs and IV line.

In an illustrative embodiment each separate fluid pump includes a pressurized reservoir or fluid chamber formed by an elastomeric membrane permanently stretched into a region of nonlinear elasticity. Such a fluid pump is disclosed in copending U.S. Patent Application entitled "Portable Infusion Pump" and commonly owned by the Assignee of the present application. This type of pump is characterized by a substantially constant fluid delivery pressure and by a substantially complete discharge of fluid from the pumping chamber. For a SASH process four separate pumps may be provided to pressurize and deliver fluid at four different substantially constant pressures. For a SAS process three pumps are required. Alternately, in place of four separate pumps a single pump having four separate chambers each pressurized to a different pressure by a single elastomer formed with areas of different thicknesses, corresponding to the different chambers may be provided.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a perspective view of a portable infusion apparatus constructed in accordance with the invention shown operatively connected to a patient;

FIG. 2 is an isometric view of a portable infusion apparatus constructed in accordance with the invention;

FIG. 3 is a schematic diagram of a portable infusion apparatus constructed in accordance with the invention;

DESCRIPTION OF PREFERRED EMBODIMENTS

Figure 4:
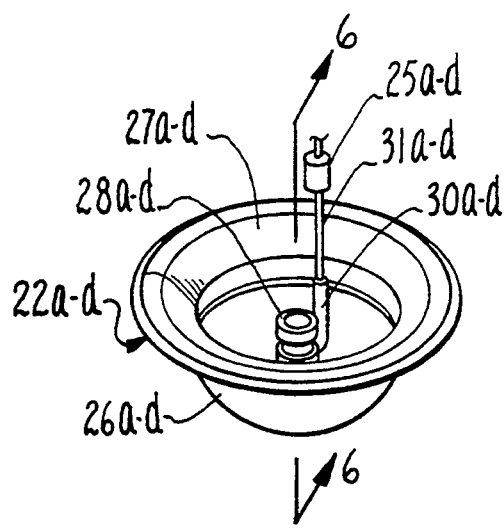
FIG. 4 is a perspective view of a single pump of the portable infusion apparatus.

Referring now to FIG. 1, an infusion apparatus for infusing medical solutions in accordance with the invention is shown and generally designated as 10. As indicated in FIG. 1 the infusion apparatus 10 may be worn by a patient 12 during ambulation and can be attached to the patient 12 by any well known means, such as a belt 14. Further, FIG. 1 shows that the infusion apparatus 10 can be connected in fluid communication with the patient 12 for the infusion of fluids into the patient 12 through an IV line 16. It is also shown that the IV line 16 can include an in-line air filter 18 of a type well known in the pertinent art which will prevent the infusion of air to the patient 12. Additionally, an on-off valve 20 can be operatively associated with the IV line 16 to initiate or terminate the flow of fluid from the infusion apparatus 10 through the IV line 16. Although the particular on-off valve 20 which is shown in the Figures is a standard slide clamp, it is to be appreciated that any on-off valve 20 that is well known in the pertinent art will suffice for purposes of the present invention. that is well known in the pertinent art will suffice for purposes of the present invention.

Referring now to FIG. 2 the infusion apparatus 10 is shown. The infusion apparatus 10 includes four fluid pumps 22a–d mounted within a single carrier housing 24. The infusion apparatus 10 shown is adapted to perform a SASH process. Alternatively a lesser or greater number of fluid pumps 22a–d may be assembled within the carrier housing 24.

As shown schematically in FIG. 3, the fluid pumps 22a–d are coupled in flow communication to the IV line 16. Additionally, each pump 22a–d is coupled to a check valve 25a–d. The check valves 25a–b are located between the IV line 16 and the fluid pumps 22a–d to regulate a sequence of fluid flow from the fluid pumps 22a–d. Each fluid pump 22a–d is adapted to deliver fluid at a substantially constant pressure until the pump 22a–d is substantially completely discharged.

Delivery pressure bands, $P_1$ through $P_4$, of the pumps 22a–d are selected such that $P_1$ band, corresponding to pump 22a is greater than $P_2$ band corresponding to pump 22b. Likewise $P_2$ band is greater than $P_3$ band corresponding to pump 22c band and $P_3$ band is greater than $P_4$ band corresponding to pump 22d. ($P_1$ band > $P_2$ band > $P_3$ band > $P_4$ band).

As used herein the terms $P_1$, $P_2$, $P_3$ and $P_4$, refer to a delivery pressure band. $P_1$, $P_2$, $P_3$ and $P_4$ are not discreet values but bands of pressure which includes the difference in start to finish discharge and the manufacturing tolerances of the fluid pump 22a–d.

The check valves 25a–d are each constructed to open at a preselected low differential pressure $\Delta P$ sensed between the downstream pressure in the IV line 16 and an upstream pressure determined by the pump delivery pressure of a fluid pump 22a–d. The check valves 25a–d can thus be constructed and arranged to allow fluid flow sequentially from pump 22a at pressure $P_1$, pump 22b at Pressure $P_2$, pump 22c at pressure $P_3$, and pump 22d at pressure $P_4$.

The infusion apparatus 10 is thus constructed to operate in a SASH process that includes the steps of:

1. connecting a first reservoir with a dosage of a saline solution, a second reservoir with a dosage of an antibiotic solution, a third reservoir with a dosage of a saline solution, and a fourth reservoir with a dosage of a heparin solution, to an IV line; and
2. sequentially discharging a dose of saline from the first reservoir at a pressure of $P_1$, a dose of antibiotic from the second reservoir at a pressure of $P_2$, a dose of saline from the third reservoir at a pressure of $P_3$, and a dose of heparin from the fourth reservoir at a pressure of $P_4$ with $P_1 > P_2 > P_3 > P_4$.

A suitable fluid pump 22a–d for pumping or discharging fluid solutions at a substantially constant pressure is shown in FIGS. 4, 5, 6A and 6B. In general each of the fluid pumps 22a–d will be of the same construction but the pumps will be sized differently. For example each pump 22a–d may be sized to contain a predetermined volume or dosage of solution which may be different. As an example the volumetric capacity of a pump 22a–d may be in the range of 20–250 ml for an antibiotic and 3–5 ml for saline depending on a required dosage. It is anticipated that the pump will be charged with a solution at the pharmacy although it is contemplated that a patient may charge some solutions.

With reference to FIG. 4 a pump 22a–d is shown. Each pump 22a–d includes a housing 27a–d. An elastomeric membrane 26a–d is clamped between rings 40a–d and 44a–d and is then attached to the housing 27a–d and to a shell (not shown), or to the carrier housing 34. FIG. 4 also shows that the housing 27a–d is formed with an inlet port 28a–d and an outlet port 30a–d. Each outlet port 30a–d of the pumps 22a–d is coupled to an outlet conduit 31a–d which in turn is coupled to the IV line 16. Each check valve 25a–d is located in an outlet conduit 31a–d situated between the outlet port 30a–d of a pump 22a–d and the IV line 16. The individual components of a pump 22a–d, however, are best seen in FIG. 5.

Figure 5:
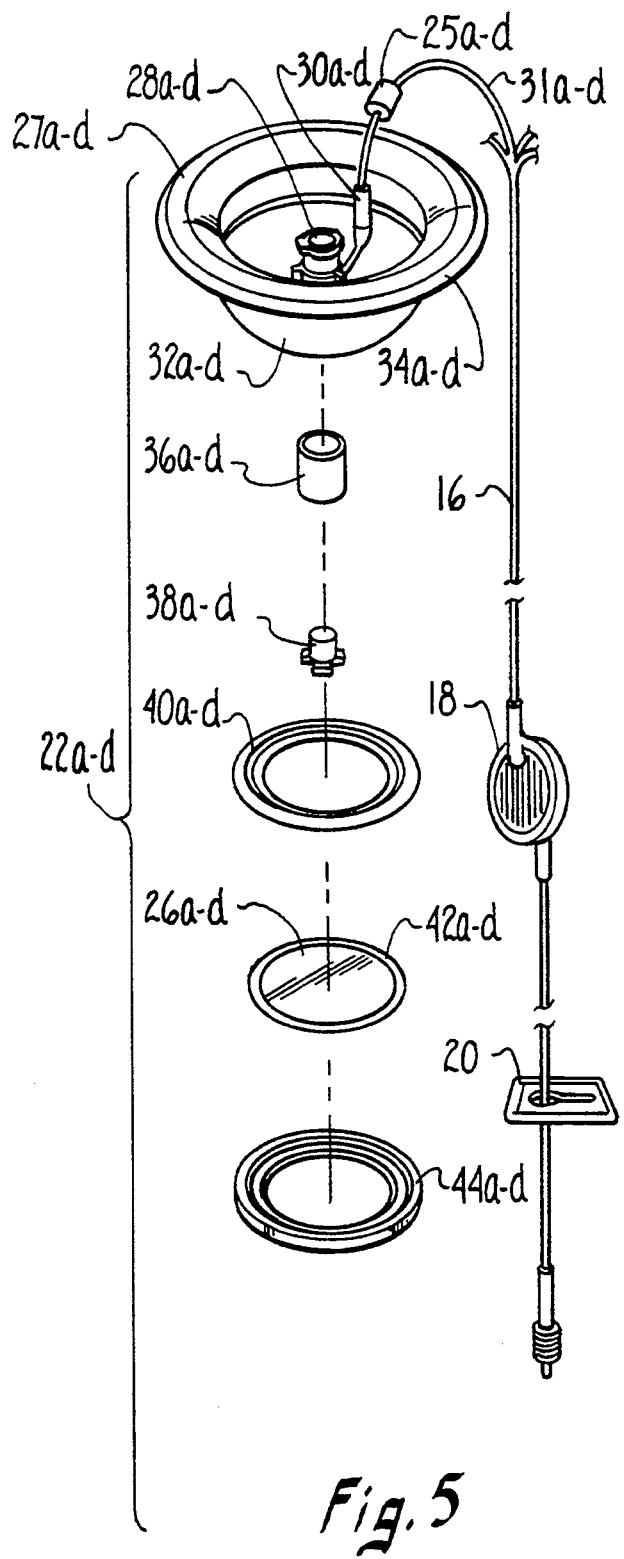
FIG. 5 is an exploded isometric view of the components of a single pump of the portable infusion apparatus.

In FIG. 5 the various components of a pump 22a–d are shown in an exploded isometric and are arranged generally in the order in which they are to be assembled. Preferably, the housing 27a–d is made of a hard plastic, such as polycarbonate, and is of a material which is chemically compatible with the fluid to be infused into the user 12. For purposes of the present invention, a contour surface 32a–d of housing 27a–d can have any topology which will stretch the membrane 26a–d into its nonlinear region of elasticity when these components are assembled. Preferably, however, the contour surface 32a–d of housing 27a–d will follow and conform to the natural topology of the inflated membrane 26a–d as it transitions from linear to non-linear. For the case shown in the Figures, contour surface 32a–d is substantially hemispherical. On the other hand, as shown in the Figures, the periphery 34a–d of housing 27a–d is folded outwardly from the contour surface 32a–d in order to facilitate the connection of the membrane 26a–d onto the housing 27a–d. The housing 27a–d can be manufactured using any well known manufacturing procedures, such as injection molding.

A thin wall tube which forms valve sleeve 36a–d, and a valve insert 38a–d are shown in FIG. 3 in their positions for insertion into the lumen of inlet port 28a–d. When inserted into the lumen of inlet port 28a–d, the sleeve 36a–d and valve insert 38a–d establish a one-way valve for the housing 27a–d which permits the flow of fluid in only one direction through the inlet port 28a–d. Specifically, it is important that each fluid pump 22a–d will be filled with fluid through the inlet port 28a–d of each chamber but that fluid not be able to leave the fluid pump 22a–d through the inlet port 28a–d. A fluid may be loaded into an inlet port 28a–d under pressure utilizing a medical syringe (not shown). Additionally, it is important that during filling of the separate fluid pumps the sequence of filling be accomplished from the highest to the lowest pressures.

Each pump 22a–d also includes an upper top ring 40a–d which is engageable with a rib 42a–d that is located on the circumference of membrane 26a–d. Upper ring 40a–d is also engageable with a lower bottom ring 44a–d to effectively grip and hold the rib 42a–d of membrane 26a–d between the rings 40a–d and 44a–d. These rings 40a–d and 44a–d can be of any suitable rigid material such as polycarbonate which, when the rings 40a–d and 44a–d are joined together to support the flexible membrane 26a–d, will provide a firm foundation for the membrane 26a–d.

With specific regard to the membrane 26a–d, it is seen in FIG. 3 that the membrane 26a–d is substantially a circular sheet when in its unstretched condition. Further, this sheet is formed with a raised rib 42a–d which, as mentioned above, can be gripped between the rings 40a–d and 44a–d. Although it will be appreciated that most elastomeric materials may be suitable for the purposes of the present invention, the membrane 26a–d is preferably made of a natural rubber or isoprene having a high elastic memory. Regardless of the particular material used for membrane 26a–d, however, it is important that the membrane 26a–d be chemically compatible with the fluid medicament which is to be infused to the user 12 from each pump 22a–d. If there is no compatibility between the membrane 26a–d and the fluid medicament a drug barrier needs to be created between the two. To establish such a drug barrier, the membrane 26a–d can be appropriately coated so that the particular surface of membrane 26a–d which is to be placed in contact with the contour surface 32a–d of housing 27a–d will not chemically interact with the fluid medicament in the pump 22a–d. Alternatively, though not shown in the Figures, a medicament compatible membrane can be held with the membrane 26a–d between the rings 40a–d and 44a–d. With this combination, the medicament compatible membrane is positioned between the membrane 26a–d and the contour surface 32a–d of housing 27a–d when these components are assembled. For purposes of the present invention, the portion of membrane 26a–d which is circumscribed by the rib 42a–d is preferably of uniform thickness. It is recognized, however, that thickness may be varied across the membrane 26a–d as long as the resultant topology creates a nonlinear elastomeric behavior for the membrane 26a–d. In addition, the thickness of the membranes 26a–d will in part be different for each pump 22a–d for achieving a different operating pressure for each pump 22a–d.

Figure 6A:
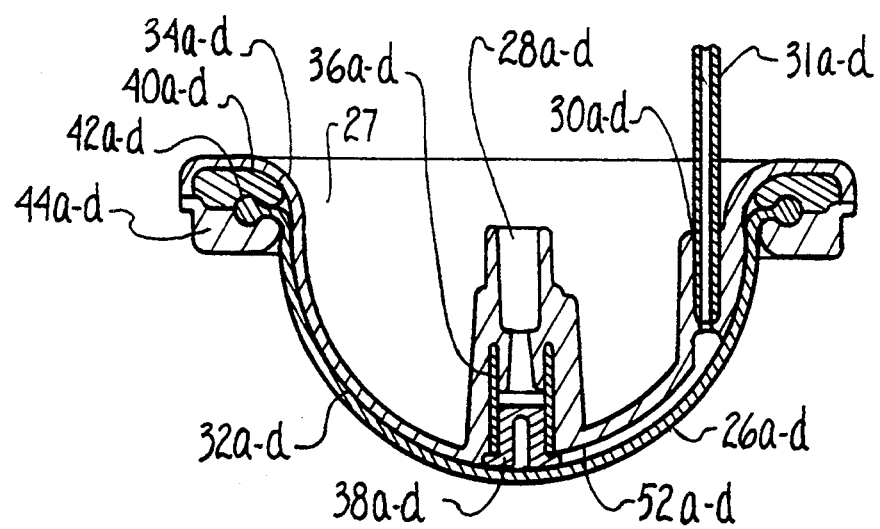
FIG. 6A is a cross sectional view of a single pump of the portable infusion apparatus as seen along line 6—6 in FIG. 5 with an elastomeric membrane of the pump collapsed.
Figure 6B:
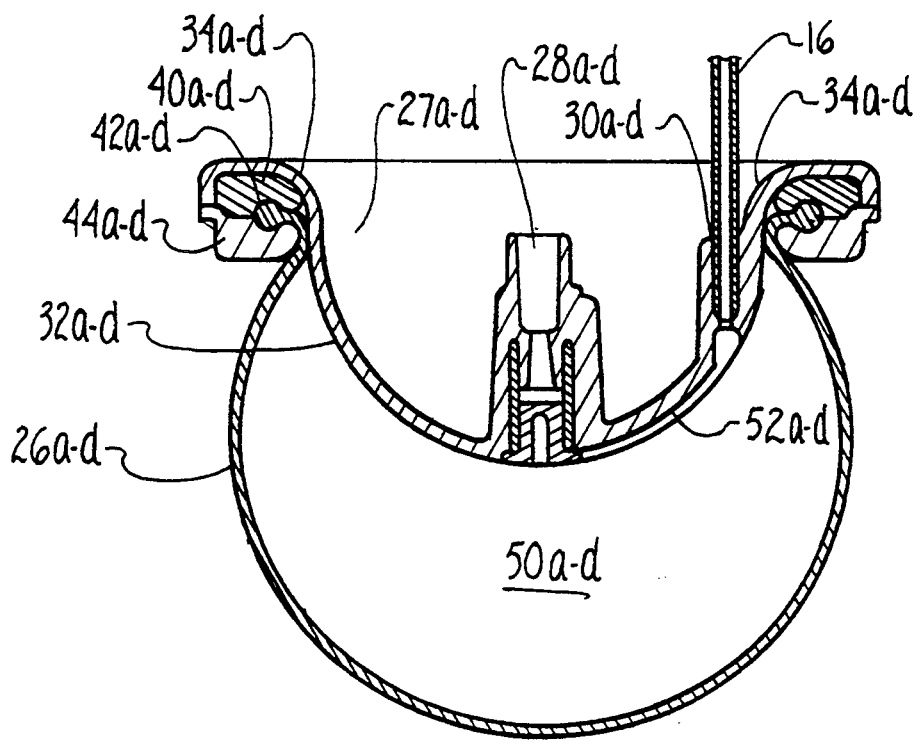
FIG. 6B is a cross sectional view of a single pump of the portable infusion apparatus as seen in FIG. 6A with the elastomeric membrane of the pump expanded to establish a pressurized fluid chamber.

The cooperation of the various structural elements of each pump 22a–d will be best appreciated with reference to both FIGS. 6A and 6B. First, in FIG. 6A it is seen that the upper top ring 40a–d is joined to the lower bottom ring 44a–d to grip and hold rib 42a–d of membrane 26a–d therebetween. The rings 40a–d and 44a–d can be joined together by any of several means, such as ultrasonic welding or solvent bonding. Additionally, as seen in FIG. 6A, the periphery 34a-d of housing 27a-d is joined to upper top ring 40a-d. When housing 27a-d is joined to upper top ring 40, the contour surface 32a-d of housing 27a-d stretches membrane 26a-d substantially as shown. Importantly, the dimensions of both membrane 26a-d and contour surface 32a-d are such that this stretching takes the membrane 26a-d into its nonlinear region of elasticity. The joining of housing 27a-d to upper top ring 40a-d also establishes a potential chamber or reservoir 50a-d between the membrane 25a-d and contour surface 32a-d.

Referring now to both FIGS. 6A and 6B, it can be appreciated that as fluid is introduced through the inlet port 28a-d of housing 27a-d and into the potential chamber 50a-d under the pressure of a syringe, or some other pumping means, any air in the system will first be vented to the outlet port 30a-d along the indentation 52a-d which is formed into contour surface 32a-d. This, of course, always happens when the air pressure is less than the pressure necessary to distend the membrane 26a-d. Then, with outlet port 30a-d blocked to prevent the flow of liquid medicament from chamber 50a-d, the elastomeric membrane 26a-d will begin to expand as additional liquid medicament is introduced into the potential chamber 50. It is important to the present invention that in order to create a substantially constant fluid pumping pressure in the chamber 50a-d, the expansion, and subsequent contraction, of membrane 26a-d be entirely accomplished with the exception of the last or lowest pressure fluid pump 22d while membrane 26a-d is in its nonlinear region of elasticity. As previously stated the elastomeric membrane 26a-d is initially stretched into its nonlinear region of elasticity during assembly of each pump 22a-d. It can be appreciated that during subsequent loading of a fluid into chamber 50a-d, a pump means such as a medical syringe must overcome the force which is exerted by the elastomeric membrane 26a-d. There must then be additional non-linear stretching of the membrane 26a-d to form and expand the chamber 50a-d as shown in FIG. 6B.

Viewed from an energy standpoint, a fluid must be introduced under a pressure sufficient to overcome the potential energy of the initially stretched membrane 26a-d and form the chamber 50 a-d. This total amount of energy minus what has been lost through heat loss and elastomeric hysteresis is thus available for displacing fluid from the chamber 50a-d at a substantially constant delivery pressure. Further, because of the initial non-linear stretching of the membrane 26a-d, even after complete discharge of a fluid, a residual force is maintained by the membrane 26a-d acting upon the contour surface 32a-d.

As previously stated each pump 22a-d must be sized to deliver a predetermined volume of fluid solution over a substantially constant predetermined delivery pressure. A size of the pump 22a-d may thus be adjusted to achieve a predetermined volume. For achieving a predetermined delivery pressure a thickness of the elastomeric membrane 26a-d as well as the material may be selected as required.

In general, the delivery pressure of a pump 22a-d will vary with the thickness of the elastomeric membrane 26a-d. Likewise the delivery pressure will vary with the modulus of elasticity of the material selected for the elastomeric membrane 26a-d.

Figure 7A:
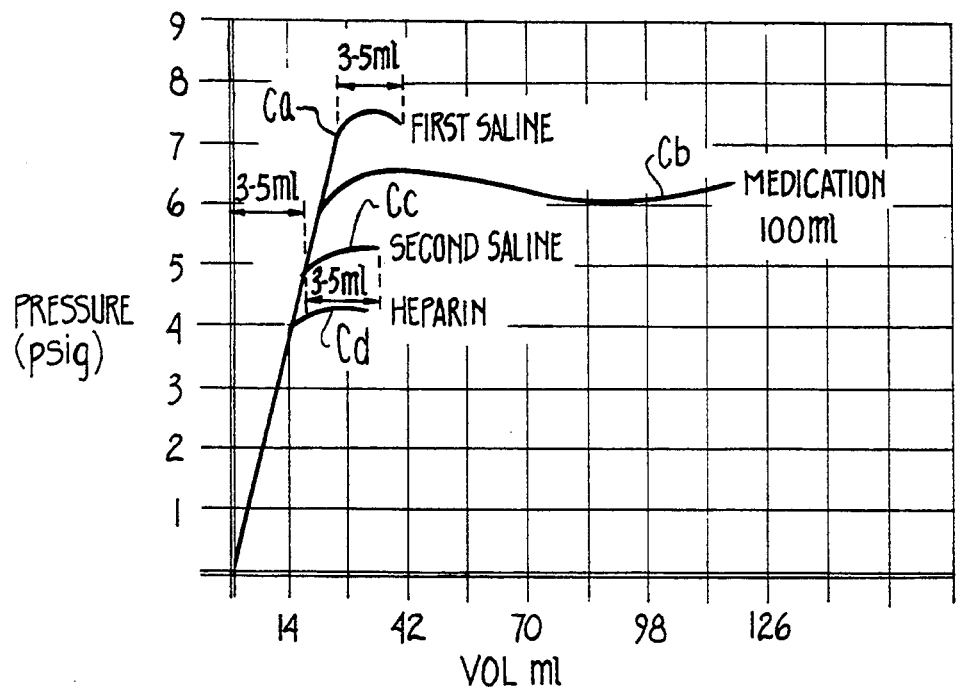
FIG. 7A is a modeled and empirically obtained Pressure versus Volume graph for the separate pumps of the infusion apparatus.
Figure 7B:
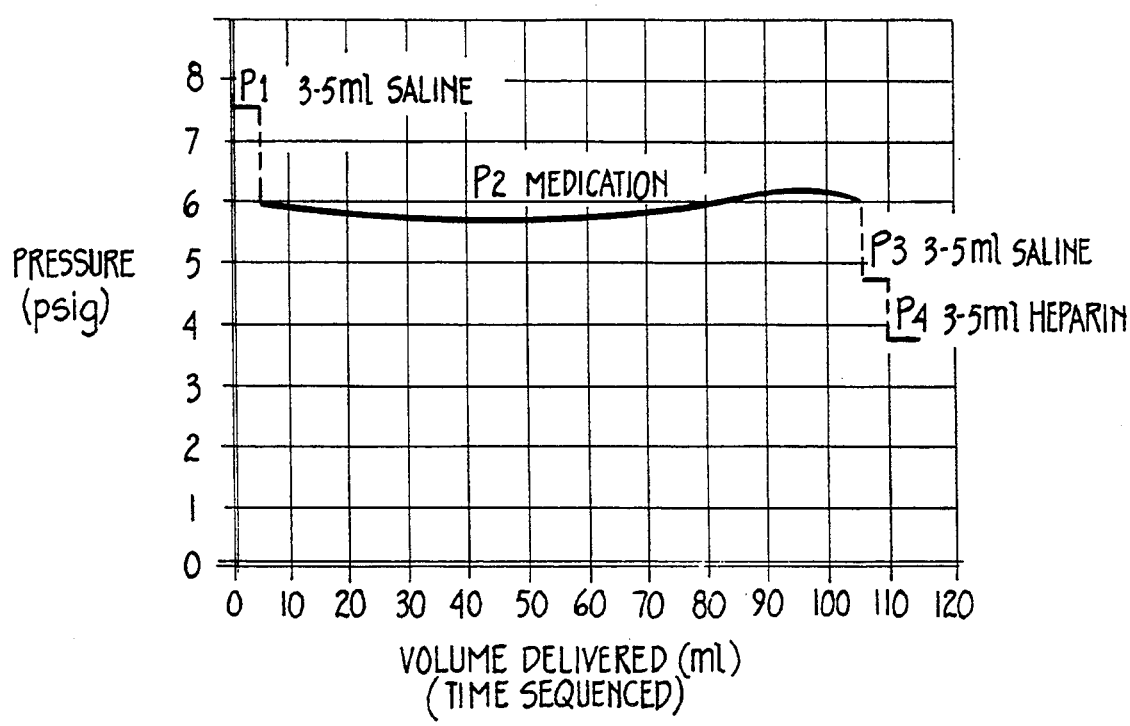
FIG. 7B is a Pressure v. Volume Delivered graph showing the discharge of fluids in a SASH process in a timed sequence.

FIGS. 7A and 7B illustrate representative volume versus pressure characteristics of the four fluid pumps 22a-d. Curves $C_{a-d}$ of FIG. 7A illustrate the volume versus pressure characteristics of pumps 22a-d respectively. In general each pump 22a-d is constructed to deliver fluid over a relatively constant pressure band. As is apparent pump 22a operates at the highest pressure band followed by pump 22b, 22c and 22d respectively. These operating pressures correspond to the operating pressures or pressure bands $P_1 > P_2 > P_3 > P_4$ shown in FIG. 3. An illustrative range of pressures may be in the range of 1-20 psig. FIG. 7B illustrates a volume delivered by the separate chambers over a time sequence.

Figure 8:
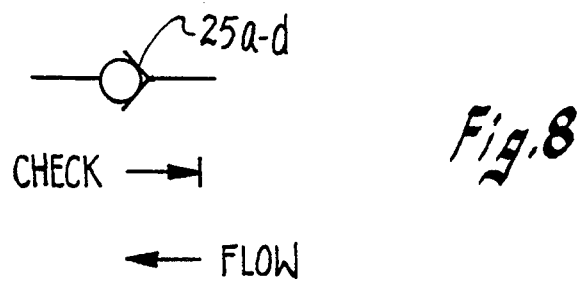
FIG. 8 is schematic diagram of a check valve component for the infusion apparatus.

The check valves 25a-d for each pump 22a-d must be configured to crack with a relatively small pressure differential $\Delta P$ between the respective operating pressures $P_1$-$P_4$ for the pumps 22a-d. Such check valves 25a-d are commercially available and in general function as shown in the schematic illustration of FIG. 8. Additionally, the check valve 25a downstream of pump 22a may be eliminated if desired.

In addition the configuration noted in FIG. 2 with four separate fluid pumps 22a-d may also be varied, as long as four separate reservoirs or chambers each at a different pressure are provided. As an example, a single pump having a single elastomeric membrane that covers a plurality of juxtaposed chambers may be provided. The thickness of the elastomeric membrane may be varied to provide a pressure differential between the separate chambers.

Figure 9:
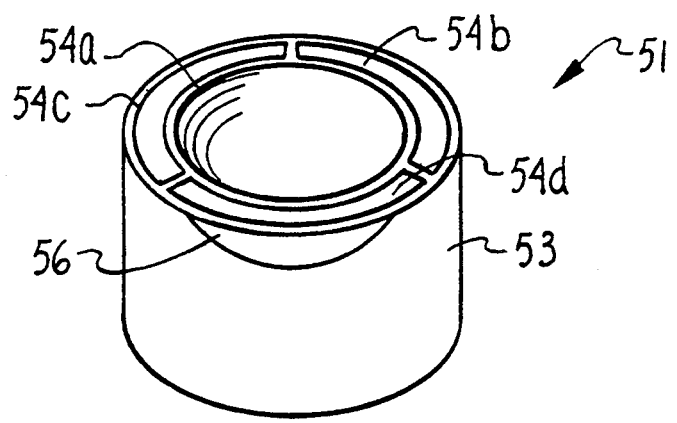
FIG. 9 is a schematic view of an alternate embodiment portable infusion apparatus.

FIG. 9 illustrates such an alternative embodiment infusion apparatus. Alternate embodiment infusion apparatus 51 includes a housing 53 having a plurality of contour surfaces 54a-d formed thereon. A single concentric elastomeric membrane 56 is mounted in operative alignment with the contour surfaces 54a-d substantially as described for elastomeric membrane 26a-d. Concentric elastomeric membrane 56 is formed however, with a varying thickness for providing chambers corresponding to contour surfaces 54a-d. The pumping or delivery pressure from each chamber can thus be varied as required.

Figure 10:
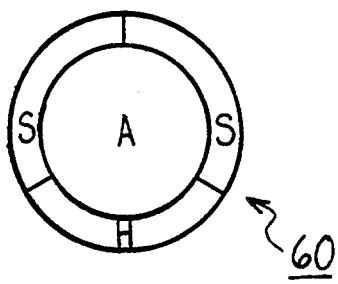
FIGS. 10 and 10A are plan views of another alternate embodiment portable infusion apparatus for a SAS sequence.
Figure 10A:
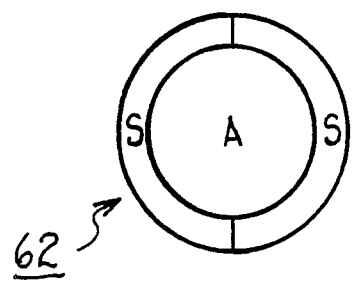

As shown in plan view in FIG. 10 a single infusion apparatus 60 for a SASH process may include four separate chambers S,A,S,H, concentrically arranged and divided. FIG. 10A illustrates a single infusion apparatus 62 having three separate and concentrically arranged chambers (S,A,S). In either case the largest chamber (A) is in the center.

Figure 11:
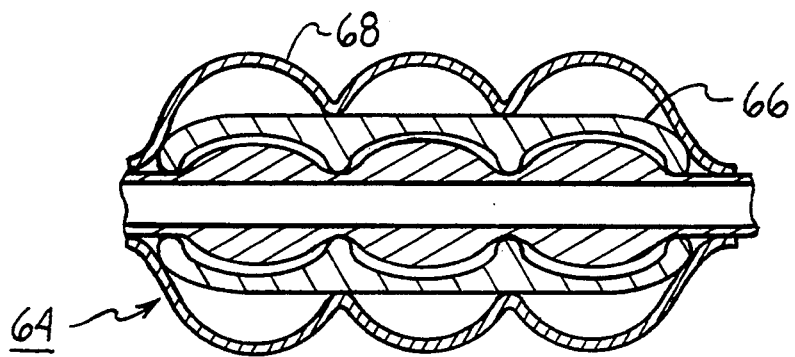
FIG. 11 is a schematic view of yet another alternate embodiment portable infusion apparatus having a generally cylindrical construction.

FIG. 11 illustrates yet another infusion apparatus 64 formed with a shell 68 and separate chambers formed by a single elastomeric membrane 66. The shell 66 may be sized to contain a fixed volume for each separate chamber.

Thus the invention provides a method and apparatus for infusing a plurality of medical solutions in a controlled sequence. The apparatus of the invention is simple in construction and may operate automatically in a SASH process. Moreover the method and apparatus of the invention is suitable for use by a mobile or ambulatory patient.

While the particular portable IV infusion apparatus as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. An infusion apparatus for infusing at least two or more different medical fluids comprising:
   a first reservoir, a second reservoir, a third reservoir and a forth reservoir wherein each said reservoir has an interior for containing one of said medical fluids;
   means for pressurizing said first reservoir to a first pressure, said second reservoir to a second pressure, said third reservoir to a third pressure and said forth reservoir to a forth pressure such that the first pressure is greater than the second pressure, said second pressure being greater than the third pressure, said third pressure being greater than the forth pressure;
   said means for pressurizing comprising an elastomeric membrane;
   means for connecting said interior of each said reservoir to a single IV conduit; and
   means for connecting said IV conduit to a patient.

2. An infusion apparatus as defined in claim 1 wherein each pumping means further comprises:
   means for stretching the membrane into its region of nonlinear elasticity;
   means for mounting the membrane on said stretching means to create a potential fluid chamber therebetween; and
   means for expelling fluid from the potential chamber by nonlinear contraction of the membrane while the membrane remains in the region of nonlinear elasticity.

3. An infusion apparatus as recited in claim 2 wherein the stretching means is a housing formed with a surface having a periphery and a predetermined contour circumscribed by the periphery and wherein the elastomeric membrane is attached to said periphery over the contour.

4. An infusion apparatus as defined in claim 1 further comprising valving means for sequentially completely discharging fluid from the first reservoir then the second reservoir then the third reservoir and then the fourth reservoir.

5. A method for infusing medical solutions in a SASH process comprising:
   pressurizing with an elastomeric membrane a first reservoir for a fluid saline solution to a pressure band of $P_1$, a second reservoir for a fluid antibiotic solution to a pressure band of $P_2$, a third reservoir for a fluid saline solution to a pressure band of $P_3$, and a fourth reservoir for a fluid heparin solution to a pressure band of $P_4$, with $P_1 > P_2 > P_3 > P_4$ wherein said pressurizing the first, second, third, and fourth reservoirs is with a elastomeric membrane by nonlinear contraction of the membrane while the membrane remains in a region of nonlinear elasticity, and further wherein said pressures $P_1$, $P_2$, $P_3$ and $P_4$ are controlled by a predetermined thickness of the elastomeric membrane;
   connecting each reservoir in flow communication to an IV line for a patient;
   discharging fluid sequentially from the first reservoir, then the second reservoir, then the third reservoir, and then the fourth reservoir with each reservoir substantially discharged of fluid prior to a next reservoir discharging fluid wherein the discharge from each reservoir but the forth reservoir is at a substantially constant pressure and said discharge is sequential by sensing a pressure differential between reservoirs for sequentially valving the reservoirs.

6. The method as recited in claim 5 wherein:
   the elastomeric membrane is stretched over a contour surface substantially hemispherical in shape.

7. The method as recited in claim 5 wherein:
   different elastomeric membranes are utilized for each reservoir and the pressures $P_1$, $P_2$, $P_3$ and $P_4$ are controlled by a modulus of elasticity of the elastomeric membrane.

8. The method as recited in claim 5 wherein the pressures $P_1$, $P_2$, $P_3$ and $P_4$ are controlled by a pre-determined thickness and modulus of elasticity of the elastomeric membrane.

9. An infusion apparatus for infusing medical fluids comprising:
   a first, a second, a third, and a fourth pumping means for pumping fluids at substantially constant pressure bands of $P_1$, $P_2$, $P_3$ and $P_4$ respectively from a first, a second, a third and a fourth chambers with $P_1 > P_2 > P_3 > P_4$ wherein said chambers are formed on a single housing, a single membrane of a varying thickness covers the reservoirs and each said pumping means comprises means for stretching the membrane into its region of nonlinear elasticity, means for mounting the membrane on said stretching means to create a potential fluid chamber therebetween, and means for expelling fluid from the potential chamber by nonlinear contraction of the membrane while the membrane remains in the region of nonlinear elasticity;
   means for mounting and coupling said pumping means to an IV conduit; and
   valving means for sequentially completely discharging fluid from the first then the second then the third, and then the fourth chambers.

10. An infusion apparatus as recited in claim 9 wherein the stretching means is a housing formed with a surface having a periphery and a predetermined contour circumscribed by the periphery and wherein the elastomeric membrane is attached to said periphery over the contour.

11. An infusion apparatus as defined in claim 10 and wherein:
    the valving means comprises three check valves located between the second, third and fourth pumping means and the IV line.

12. An infusion apparatus as defined in claim 9 wherein:
    the chambers are concentrically arranged and divided.

13. An infusion apparatus as defined in claim 9 wherein:
    the chambers are formed by a cylindrical shell separated into separate chambers by the elastomeric membrane and sized to contain a fixed volume per chamber.

* * * * *